United States Patent [19]

Knuuttila et al.

[11] Patent Number: 4,952,546
[45] Date of Patent: Aug. 28, 1990

[54] CATALYST SYSTEM FOR SELECTIVE ALKYLATION OF TOLUENE

[75] Inventors: Pekka Knuuttila, Porvoo; Erkki Halme, Helsinki; Leila Lahtinen, Helsinki; Salme Koskimies, Helsinki, all of Finland

[73] Assignee: Neste Oy, Finland

[21] Appl. No.: 235,886

[22] PCT Filed: Dec. 29, 1987

[86] PCT No.: PCT/FI87/00174
§ 371 Date: Aug. 11, 1988
§ 102(e) Date: Aug. 11, 1988

[87] PCT Pub. No.: WO88/04955
PCT Pub. Date: Jul. 14, 1988

[30] Foreign Application Priority Data

Dec. 31, 1986 [FI] Finland .................................. 865362

[51] Int. Cl.$^5$ .................. B01J 21/02; B01J 23/10; B01J 23/14; B01J 27/232
[52] U.S. Cl. ..................................... 502/174; 585/452; 585/467
[58] Field of Search ................. 502/174; 585/452, 467

[56] References Cited

U.S. PATENT DOCUMENTS

| 3,260,679 | 7/1966 | O'Grady et al. | 585/601 X |
| 3,756,963 | 9/1973 | Forni | 502/174 X |
| 4,609,637 | 9/1986 | Drake | 502/174 |

FOREIGN PATENT DOCUMENTS

| 0169568 | 1/1986 | European Pat. Off. . |
| 1269280 | 4/1972 | United Kingdom . |
| 1419445 | 12/1975 | United Kingdom . |

Primary Examiner—W. J. Shine
Attorney, Agent, or Firm—Steinberg & Raskin

[57] ABSTRACT

The object of the invention is a catalyst system for selective alkylation of toluene with propylene. The catalyst system contains metallic sodium on a $K_2CO_3$ carrier and transition metal oxide, which advantageously is $CeO_2$, $Dy_2O_3$ or $Fe_2O_3$, as promoter. The invention also concerns a procedure for selective alkylation of toluene with propylene in the presence of a catalyst system.

6 Claims, No Drawings

CATALYST SYSTEM FOR SELECTIVE ALKYLATION OF TOLUENE

BACKGROUND OF THE INVENTION

The invention concerns a catalyst system and procedure for selective alkylation of toluene.

There are two main methods to industrially produce alkylbenzene. One if Friedel-Crafts alkylation, which has the drawback that it tends to lead to polysubstitution (ring substitution) and, thereby, to difficult separation problems.

The other method uses base catalysts, such as Li, Na or K metals in the reaction between aromatic hydrocarbons and olefines. It is usual practice to use e.g. a $K_2CO_3$ carrier. An efficient side chain alkylating catalyst is obtained when metallic sodium is dispersed on the surface of dry potassium carbonate. An alkali metal catalyst produces a smaller number of different isomers than a Friedel-Crafts catalyst. The drawback is the comparatively low selectivity of the alkali metal catalyst to aromatics and its tendency to produce various isomers of alkylbenzene, which are hard to separate. Aliphatic dimers are also formed, although these are easily separated from alkylbenzene by distillation.

The selectivity of an alkyl metal catalyst is lowered at the preparation stage by oxygen and water residues in the $K_2CO_3$ carrier, whereby oxides and hydroxides are formed from part of the active metal. It is for this reason necessary to dry the carrier well at 120°-150° C. in vacuum for 10-20 hours and to prepare the catalyst in an inert atmosphere or in vacuum.

The x-ray diffraction spectrum run on unused catalyst reveals the presence of the following phases on the surface of the catalyst: $Na_2O$, $K_2O$, $K_2CO_3$, K, and only a minor quantity of metallic Na and liquid, amorphous Na/K alloy, although the diffraction from the latter cannot be observed. Thus the catalyst has to be prepared in inert conditions in order to avoid oxidation. The alkali metal should be added in single doses as small as possible with the aid of a sodium press, or dispersed in an appropriate solvent; adequate dispersion is ensured in this way.

For improving the activity and selectivity of the $Na/K_2CO_3$ alkylation catalyst, various organic promoters may be used, such as butadiene, anthracene, graphite, heterocyclic nitrogen compounds (methylpyridines) and "acetylenic hydrocarbons", and oxygenous hydrocarbons. The effect of organic promoters has been said to be based on formation of a complex between metallic potassium and the promoter, and this complex would have higher activity than the alkali metal alone. The stability of such a complex in the reaction conditions applied (>150° C.) is however unlikely. Various, better results have been achieved using inorganic promoters: for instance metallic copper, cobalt, titanium and ground steel have been tried. It is clearly observable that promoters of various characters exert an effect on alkylation and dimerization.

Catalysts like the catalyst of the invention are known in the art from other connections. As state of art is cited U.S. Pat. No. 3,260,679, in which a catalyst system is disclosed which contains metallic sodium on an aluminum oxide carrier. As promoter for the metallic sodium serves a transition metal compound, advantageously an oxide. In the preparation of this catalyst, the sodium is added onto the aluminium oxide carrier, the carrier being first heated in a dry atmosphere to about 200°-600° C. The sodium is added in fine powder form. The mixture is then agitated, whereby the sodium disperses on the surface of the aluminium oxide carrier. For transition metal oxide, in the reference iron oxide $FeO_3$ is used. The impurities present in the catalyst have to be removed in order to attain sufficient life span of the catalyst. Use of these catalysts has been reported e.g. in conversion of 1-alkenes into 2-alkenes.

SUMMARY OF THE INVENTION

The object of the invention is a procedure by which the base catalyst used towards alkylating toluene with propylene is modified in order to improve the activity, or yield, and selectivity of the catalyst. More specifically, the aims of the invention are: to increase the proportion of the desired product IBB (isobutylbenzene) in the reaction

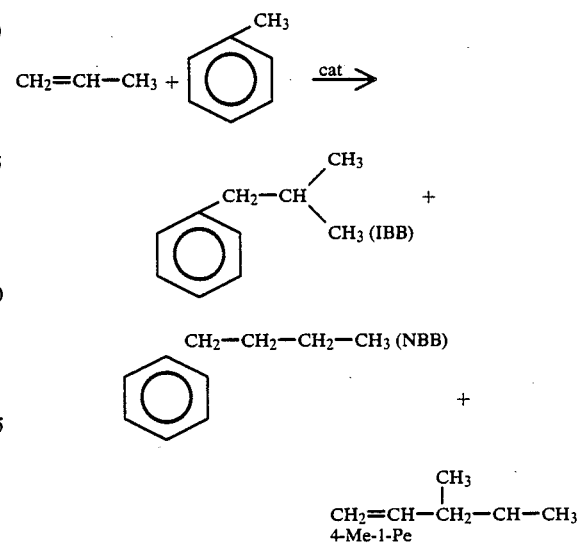

at the expense of the principal by-products 4-Me-1-Pe (4-methyl-1-pentene) and NBB (butylbenzene).

An influence can also be exerted on the dimerization reaction

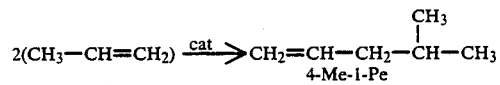

by modifying the catalyst of the invention and by using the correct amount thereof.

The catalyst system is mainly characterized in that it contains metallic sodium on a $K_2CO_3$ carrier, and a transition metal oxide as promoter.

The transition metal oxides used in the invention are advantageously cerium, dysprosium and iron oxide.

DESCRIPTION OF THE PREFERRED EMBODIMENTS

In the procedure of the invention the promoters increase the selectivity to isobutylbenzene or, on the other hand, to 4-methyl-1-pentene and the activity of the catalyst. Promoters of the invention are preferably transition metal oxides, or advantageously $CeO_2$, $Dy_2O_3$ and $Fe_2O_3$.

The catalyst has for instance been prepared in a Schlenk glass vessel, in which case vacuum and nitrogen flushing may be used in aid. In this case only relatively small catalyst quantities at a time can be safely manufactured.

The problem has been how to provide efficient agitation in the glass system; and use of high enough temperature is necessary. The most efficient catalyst was obtained when the temperature was 200°–250° C.

For this reason catalyst was also prepared in a steel mixer, in which at a time about 500 g of the catalyst could be manufactured, and which has efficient mechanical agitation.

The promoter is advantageously added to the catalyst at the reactor charging stage. The quantity of promoter is preferably 1 to 5% of the catalyst quantity. The quantity of sodium is preferably 5% of the $K_2CO_3$ quantity.

The alkylation reaction may be implemented as a charge, semi-charge or continuous process at temperature 100°–200° C., preferably 140°–160° C., and pressure 10–100 bar, preferably 40–70 bar. High pressure favours dimerization of propylene. The proportion of olefine and aromate input may vary in the range from 10 to 0.5, preferably from 6 to 2. Higher ratios favour dimerization of olefine, while lower ratios accelerate the quantity of alkylbenzenes. The semicharge process is carried out under constant propylene pressure, and continuous propylene input to the reactor is provided. The reaction takes place in the aqueous phase. It is thus understood that the total pressure is constant and it is maintained with propylene.

The diffraction spectrum run on the catalyst shows that the sodium dispersed on the surface of $K_2CO_3$ is almost totally bound as $Na_2O$ and as Na/K alloy and no presumed ion exchange $K_2CO_3$ to $Na_2CO_3$ takes place, at least not on the catalyst surface; the observed free K metal rather seems to originate in decomposition of carrier.

The following examples illustrate the procedure more closely.

EXAMPLES

With glass equipment, a basic catalyst was prepared, utilizing Schlenk technique, 50 g $K_2CO_3$ were weighted into a 250-ml Schlenk flask, kept in vacuum at about 230° C. over night about 16 hrs. and stored in a nitrogen chamber. Sodium pieces, washed with dry toluene, were weighted and added upon the potassium carbonate, in nitrogen atmosphere. Heating to about 200° C. and dispersion of the molten sodium with the aid of a magnetic stirrer. In all trials sodium was added about 5% of the $K_2CO_3$ quantity.

Basic catalyst manufactured in a steel mixer was prepared 500 g at a time. Efficient mechanical agitation was provided in the vessel. Vacuum could not be used in this instance, but nitrogen flushing of the vessel could be arranged. All catalysts were immediately upon manufacturing transferred into a nitrogen chamber for storage and charging into the reactor. Sodium was used about 5% of the $K_2CO_3$ quantity. When the sodium was added to the carrier with the aid of a sodium press and continuous mixing was maintained at about 250° C., and a long reaction time was used, a catalyst was obtained which was highly efficient, but the catalyst formed a hard, compact cake, which was difficult to manage, owing to different metal proportion of the K/NA alloy. In reaction conditions, however, the catalyst is in molten state.

20 g of the catalyst were charged in a one-liter Parr reactor, in the nitrogen chamber. Thereafter, 213.11 g of water-free toluene and 115.18 g propylene were weighed into the reactor. The molar proportion of propylene and toluene was 1.19. Reaction temperature was 164° C. and duration of test, 19 hrs. The pressure in the reactor was 43 bar at the beginning and 26 bar at the end.

In the examples, all promoters were added prior to charging the reactor with the catalyst.

The results are seen in Tables 1 and 2.

The tables reveal that, using the catalyst of the invention, one achieves better activity regarding IBB, or better IBB selectivity, compared with the reference examples. It should be noted that better yield automatically entails poorer selectivity. The tables also contain examples of how the promoters quantity affects the result.

TABLE 1

| | | | Catalysts prepared in metallic reactor | | | | |
|---|---|---|---|---|---|---|---|
| Run Code | Catalyst | Promoter | Promoter Quantity, [%] | IBB Select., [%] | 4-Me-1-Pe Select., [%] | NBB Select., [%] | IBB Activity, [kg/kg cat] |
| 1 | A | $CeO_2$ | 5 | 72.77 | 5.67 | 8.71 | 6.47 |
| 2 | A | $Dy_2O_3$ | 5 | 72.48 | 4.44 | 8.19 | 7.50 |
| 3 | A | $PbO_2$, $CeO_2$ | 1.25 + 1.25 | 73.16 | 6.81 | 8.19 | 5.61 |
| 4 | A | $Dy_2O_3$, $CeO_2$ | 1.25 + 1.25 | 74.68 | 4.01 | 8.32 | 6.37 |
| 5 | A | $CeO_2$ | 1.25 | 72.96 | 5.42 | 8.34 | 6.45 |
| 6 | A | $Dy_2O_3$ | 1.25 | 72.88 | 4.69 | 7.69 | 6.44 |
| 7 (Ref.) | B | $MnO_2$ | 2,5 | 73.69 | 5.79 | 8.11 | 5,26 |
| 8 (Ref.) | A | Naphthalene | 2.5 | 72.69 | 5.43 | 7.37 | 4.64 |
| 9 (Ref.) | B | (Basic cat. II) | | 73.21 | 6.03 | 7.77 | 4.14 |
| 10 (Ref.) | B | $TiO_2$ | 2.5 | 73.12 | 5.14 | 7.91 | 4.91 |

TABLE 2

| | | | Catalysts prepared in glass reactor | | | | |
|---|---|---|---|---|---|---|---|
| Run Code | Catalyst | Promoter | Promoter Quantity, [%] | IBB Select., [%] | 4-Me-1-Pe Select., [%] | NBB Select., [%] | IBB Activity, [kg/kg cat] |
| 11 | F | $Fe_2O_3$ | 2.5 | 76.03 | 5.60 | 7.78 | 4.86 |
| 12 | K | $B_2O_3$ | 2.5 | 74.78 | 4.47 | 7.57 | 5.93 |
| 13 | L | $Dy_2O_3$ | 2.5 | 70.24 | 4.63 | 7.22 | 6.24 |
| 15 | F | $Dy_2O_3$ | 5.0 | 74.39 | 4.52 | 8.05 | 4.87 |
| 16 (Ref.) | J | Naphthalene + Toluene | | 72.13 | 5.65 | 7.54 | 4.11 |

TABLE 2-continued

| | | Catalysts prepared in glass reactor | | | | | |
|---|---|---|---|---|---|---|---|
| Run Code | Cata- lyst | Promoter | Promoter Quantity, [%] | IBB Select., [%] | 4-Me-1-Pe Select., [%] | NBB Select., [%] | IBB Activity, [kg/kg cat] |
| 17 (Ref.) | K | Basic catalyst Prop./Tol. = 0.60 | | 74.63 | 3.38 | 8.30 | 5.76 |
| 18 (Ref.) | K | (Basic cat.) | | 73.72 | 4.90 | 7.49 | 5.99 |

We claim:

1. A catalyst system for selective alkylation of toluene with propylene, wherein said system contains metallic sodium on a $K_2CO_3$ carrier, and a promoter which is selected from the group consisting of $CeO_2$, $Dy_2O_3$, $PbO_2$, and $B_2O_3$.

2. The catalyst system of claim 1, wherein said promoter is $CeO_2$ or $Dy_2O_3$.

3. The catalyst system of claim 1, wherein quantity of said promoter is 1 to 5% of catalyst quantity.

4. The catalyst system of claim 1, wherein quantity of said sodium is 5% of $K_2CO_3$ quantity.

5. The catalyst system of claim 1 wherein said promoter is a mixture of $PbO_2$ and $CeO_2$.

6. The catalyst system of claim 1 wherein said promoter is a mixture of $Dy_2O_3$ and $CeO_2$.

* * * * *